(12) United States Patent
Ellingsen et al.

(10) Patent No.: US 11,047,784 B2
(45) Date of Patent: Jun. 29, 2021

(54) DEVICE AND METHOD FOR CONTINUOUS DETECTION OF CHANGES OF DENSITY IN FLUIDS AND SOLIDS AS WELL AS USE OF THE DEVICE

(71) Applicant: MECSENSE AS, Oslo (NO)

(72) Inventors: Olav Ellingsen, Oslo (NO); Bjarte Sorebo Ellingsen, Oslo (NO)

(73) Assignee: MECSENSE AS, Oslo (NO)

( * ) Notice: Subject to any disclaimer, the term of this patent is extended or adjusted under 35 U.S.C. 154(b) by 166 days.

(21) Appl. No.: 14/889,626

(22) PCT Filed: May 6, 2014

(86) PCT No.: PCT/EP2014/059204
§ 371 (c)(1),
(2) Date: Nov. 6, 2015

(87) PCT Pub. No.: WO2014/180825
PCT Pub. Date: Nov. 13, 2014

(65) Prior Publication Data
US 2016/0109346 A1    Apr. 21, 2016

(51) Int. Cl.
*G01N 9/00* (2006.01)
*G01N 29/34* (2006.01)
(Continued)

(52) U.S. Cl.
CPC ............ *G01N 9/00* (2013.01); *A61B 5/0051* (2013.01); *A61B 5/14532* (2013.01);
(Continued)

(58) Field of Classification Search
CPC ...... G01N 9/00; G01N 29/343; G01N 29/245; G01N 29/032; G01N 2291/012;
(Continued)

(56) References Cited

U.S. PATENT DOCUMENTS

| | | | | |
|---|---|---|---|---|
| 4,930,511 A | * | 6/1990 | Rossman | A61B 8/0875 600/437 |
| 5,119,819 A | * | 6/1992 | Thomas | A61B 5/14532 600/347 |
| 5,214,966 A | * | 6/1993 | Delsing | G01F 1/66 73/861.27 |

(Continued)

FOREIGN PATENT DOCUMENTS

WO      WO 03/000119      1/2003

OTHER PUBLICATIONS

Adamowski J C et al.; Ultrasonic Measurement of Density of Liquids Flowing in Tubes; IEEE Transactions on Ultrasonics, Ferroelectrics and Frequency Control, IEEE US, vol. 45, No. 1, Jan. 1, 1998; pp. 48-56, XP011437575 ISSN: 0885-3010, DOI: 10.1109/58.646909.

(Continued)

*Primary Examiner* — Xin Y Zhong
(74) *Attorney, Agent, or Firm* — Knobbe, Martens, Olson & Bear, LLP (57) ABSTRACT

The present invention relates to a sensor for continuous detection of minute changes of density in fluids and biological fluids, solids and semisolid bodies by use of a transducer.
The invention also relates to a method for continuous detection of changes of density of fluids or solids as well as use of the device.

15 Claims, 10 Drawing Sheets

(51) Int. Cl.
*A61B 5/145* (2006.01)
*G01N 29/032* (2006.01)
*A61B 5/00* (2006.01)
*A61B 8/08* (2006.01)
*G01N 29/24* (2006.01)

(52) U.S. Cl.
CPC ........ *A61B 5/14546* (2013.01); *A61B 5/4875* (2013.01); *A61B 8/08* (2013.01); *G01N 29/032* (2013.01); *G01N 29/245* (2013.01); *G01N 29/343* (2013.01); *G01N 2291/012* (2013.01); *G01N 2291/02818* (2013.01)

(58) Field of Classification Search
CPC ........ G01N 2291/02818; A61B 5/4875; A61B 5/14546; A61B 5/14532; A61B 5/0051; A61B 8/08
See application file for complete search history.

(56) References Cited

U.S. PATENT DOCUMENTS

| | | | | |
|---|---|---|---|---|
| 6,053,041 A | * | 4/2000 | Sinha | G01F 23/28 340/621 |
| 2003/0074953 A1 | * | 4/2003 | Glaser | G01N 9/24 73/32 A |
| 2003/0167848 A1 | * | 9/2003 | Glaser | G01N 9/24 73/597 |
| 2009/0277272 A1 | * | 11/2009 | Hofmann | G01N 29/032 73/632 |

OTHER PUBLICATIONS

Delsing, J. 1987 "A new velocity algorithm for sing-around-type flow meters" IEEE Transactions on Ultrasonics, Ferroelectrics and Frequency Control vol. UFFC-34, No. 4: 431-436.

* cited by examiner

Fig. 1

Figure 2 – Phase delay versus increase in density difference

Figure 3 – Depiction of the simulation setup (not to scale)

Figure 4 – Test tensor

Fig. 5 – Density Vs Phase delay at 20 °C

Fig. – 6 Temperature Vs Phase delay silver container

Fig. – 7 Density Vs Phase delay for silver container

Fig. – 8 Density Vs Phase delay for steel container

Figure 9 – Test results

DEVICE AND METHOD FOR CONTINUOUS DETECTION OF CHANGES OF DENSITY IN FLUIDS AND SOLIDS AS WELL AS USE OF THE DEVICE

FIELD OF THE INVENTION

The present invention is related to a sensor for continuous detection of minute change of density in fluids and biological fluids, solids and semisolid bodies by a transducer. The transducer used may be of different types and a PZT (Piezo Electric) transducer is preferably used. The invention is also related to a method for determining minute changes in density of fluids and biological fluids by a transducer as well as the use of such a transducer. In connection with the present application the transducer is used to register the change of density as the change of the phase shift between the exited pulse train and its reflection in addition to the amplitude difference between the two pulse trains—ingoing train and reflected train.

BACKGROUND OF THE INVENTION

Density, which is expressed as the relationship between mass and volume by the formulae $\rho = m/V$ kg/m$^3$, is normally settled by weighing a volume of the mass and divide this by the mass of the body. For a solid mass, its volume can be found by emerging the body in a liquid and measure the displacement of the liquid.

However, the density of either liquids or bodies is dependent upon its volume at a set temperature. For example water has a density of 1000 kg/m$^3$ at 4° C., but as the volume increases by increasing temperature, the density is less than 1000 kg/m$^3$ as shown in the following calculations between 4 and 10° C.:

| °C. | $T_x$ °C. | Expension coefficient γ cm$^3$/K | Volum change of water Vx = Vo*γ*(Tx − T4) + Vo | Mass g | Density ρ g/cm$^3$ | Diffence between $T_x$ and 274° K Δρ g/cm$^3$ |
|---|---|---|---|---|---|---|
| 4 | 274 | 0.0002 | 1 | 1 | 1.00000000 | 0 |
| 5 | 275 | 0.0002 | 1.0002 | 1 | 0.99980004 | 0.00019996 |
| 6 | 276 | 0.0002 | 1.0004 | 1 | 0.99960016 | 0.00039984 |
| 7 | 277 | 0.0002 | 1.0006 | 1 | 0.99940036 | 0.00059964 |
| 8 | 278 | 0.0002 | 1.0008 | 1 | 0.99920064 | 0.00079936 |
| 9 | 279 | 0.0002 | 1.001 | 1 | 0.99900100 | 0.00099900 |
| 10 | 280 | 0.0002 | 1.0012 | 1 | 0.99880144 | 0.00119856 |

Normally these minute changes in the density are neglectible, but in special cases knowing the change of density is vital. One example is in order to monitor the change in body liquids which can change by changes of the solutes in the body liquid. One such solute can be alcohol, another one can be glucose and still another one can be related to dehydration, leading to concentrating of the solutes in the body liquid. As the volume of the liquids change by changing temperature, a temperature sensor monitors the temperature of the body/liquid and displays the density at the temperature at which the measurement was taken. As a further example fresh food may be mentioned, such as meat and fruit and so forth. Bacterial growth in the fresh food will effect a change of the density of the food, and the present invention could thus function as a quality control in this case. At present no means for easy determination of minute changes in density are available.

SUMMARY OF THE INVENTION

In order to solve the above-mentioned technical problems, and provide the said means, the present invention provides a device for continuous detection of minute changes of density in fluids or solids, comprising a transducer generating pulse trains, a pulse transmitter, power input, signal analyzer and a read out unit.

According to the present invention the transducer is selected from the group consisting of a PZ (Piezo Electric) transducer, a magnetic transducer, a sound transducer, a mechnical transducer and a pneumatic transducer.

The transducer is preferably a piezo electric transducer.

The pulses generated by the transducer are selected from the group consisting of sinus pulses, square pulses and step pulses.

The pulses generated are preferably sinus pulses.

The present invention also provides a method for continuous detection of changes of density of fluids or solids, comprising applying a fixed pulse train generated by a transducer to the surface of the body/liquid in question and monitoring the change in phase shift and amplitudes between the ingoing pulses and the reflected pulses.

In a preferred embodiment of the method the transducer used is selected from the group consisting of a PZ (Piezo Electric) transducer, a magnetic transducer, a sound transducer, a mechanical transducer and a pneumatic transducer.

The transducer used is preferable a PZ transducer.

The pulse train generated in the method according to the invention is preferably selected from the group consisting of sinus pulses, square pulses and step pulses.

In a preferred embodiment the pulse train is sinus pulses.

The invention also relates to the use of the device for monitoring the change of density of body liquids caused by changes of solutes in said liquid.

One body liquid of interest is glucose.

Another body liquid of interest is alcohol.

A further condition which may be monitored is dehydration.

The present invention also relates to the monitoring of the change of density of beverages, such as wine or liquor.

Another embodiment of the invention relates to the monitoring of the change of density of wood or wood products.

A further embodiment of the invention relates to the monitoring the density of oil.

DETAILED DESCRIPTION OF THE INVENTION

According to the present invention the detection of density changes, when using a PZ tranducer, involves the detection and use of piezoelectric properties of the materials.

The key element in the technique according to the invention is that once the piezoelectric element is excited and when the excitation force is stopped it experiences the response voltage due to the reverse piezoelectric effect. The inventors have found that this response contains information that is distinguishable for different density levels.

Industrially it can be of interest to know the density of beverages at a set temperature of, such as for wine and liquor. Another example can be to monitor the moisture in for example wood, where the density of the wood and water gives the bulk density which will change depending on the water content. If the density is required at a given temperature, a mathematical algorithm compensates for the measured values if the temperature is higher/lower that the required temperature. The algorithm is based upon the following:

The general formula for the density is:

$$\rho_o = m/V_o \text{ kg/m}^3$$

wherein m=the mass of the body and $V_o$ is the volume of the body at a set temperature of $t_o$.

When the temperature increases/decreased from $t_o$ to $t_x$, the volume changes in accordance with:

$$V_x = V_o * \gamma * (T_x \pm T_o) * V_o \text{ m}^3$$

wherein $\gamma$ is the expansion coefficient for the body/liquid in question and $T_x$ is the temperature at the point of measurement.

The density of the same mass is then:

$$\rho_x = m/V_x \text{ kg/m}^3$$

The difference in density is thus:

$$\Delta\rho = \rho_o \pm \rho_x \text{ kg/m}^3$$

$$\Delta\rho = m*(1/V_o \pm 1/((V_o*\gamma*(T_x-T_o)) + V_o \text{ kg/m}^3$$

The following relationship exists between $\rho_o$ and $\rho_x$:

$$\rho_o = \rho_x * V_o / V_x \text{ kg/m}^3$$

Still another use of the invention is to monitor certain fluids in pipes, such as oil pipes whereby it is made possible to continuously monitor the real density of the oil at the actual temperature. This makes it possible to detect changes of the density caused both by the temperature and water and gas content in the oil.

A special case within the oil industry is to measure the density of the oil to establish the API grade. Normally this is done by 15.56° C. By using the present invention it is possible to measure the density at any temperature by taking into account the increased volume (or decreased volume) at the temperature.

The objective of the invention has been to find a simple principle which makes continuous monitoring of the changes of density "on site" without taking a sample of the object in question, possible.

This is achieved by applying a fixed pulse train generated by a PTZ transducer to the surface of the body/liquid in question and monitoring the change in the phase shift and amplitudes between the ingoing pulses and the reflected pulses.

The pulses used may be sinus pulses, square pulses or step pulses. The pulses may be generated electrically, mechanically, pneumatically or hydraulically.

As indicated above, one possible use of the present invention would be to monitor changes in the glucose level in a human body. Different types of sensors for this purpose have already been described. Thus U.S. Pat. No. 5,119,819 discloses a method and apparatus for non-invasive monitoring of changes in blood glucose concentration in a tissue specimen. The sensor used is based on the measurement of velocity changes of reflected ultrasound over a fixed distance with frequencies approaching 7.5 MHz, and whereby the velocity difference is due to changes of glucose content in blood combined with temperature difference. The method is in fact not non-invasive as claimed, since the sensor is to be placed on the earlobe with a tube extending through the ear lobe with the ultrasound sender attached at one end and a reflector at the other end thereof.

The objective with the invention has been to find a simple principle which continuous could monitor the changes of the density "on site" without taking a sample of the object in question.

This is achieved by applying a fixed pulse train generated by a PTZ transducer to the surface of the body/liquid in question and monitoring the change in the phase shift and amplitudes between the ingoing pulses and the reflected pulses.

Figure 2:
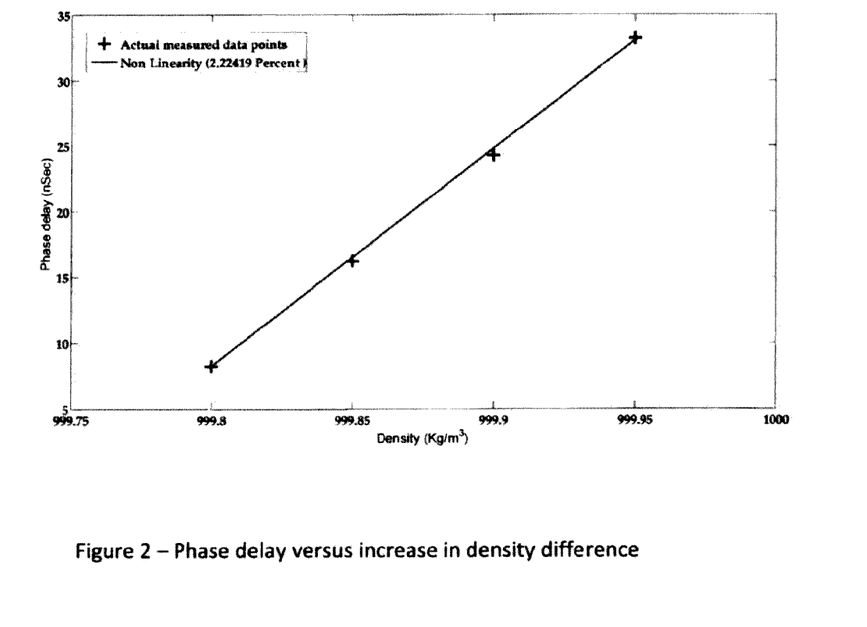
FIG. 2 is a graph showing phase delay as a function of increase in density difference.

In order to verify the principle, a mathematical simulation of the same has been performed, which gave the results as shown in the graph illustrated in FIG. 2.

From FIG. 2, it can be observed that, however small, there is a non-linearity of 2.224% in the results; this can be explained by the noise in the software setup.

The table below shows the computed phase delay between the densities in the region of interest, considering 999.80 kg/m³ as reference.

TABLE 1

Density versus phase delay in ns.

| Nr | Density (kg/m³) | Phase Delay Difference (ns) |
|---|---|---|
| 1 | 999.80-999.85 | 8.27 |
| 2 | 999.80-999.90 | 16.25 |
| 3 | 999.80-999.95 | 24.27 |
| 4 | 999.80-1000.00 | 33.20 |

Figure 3:
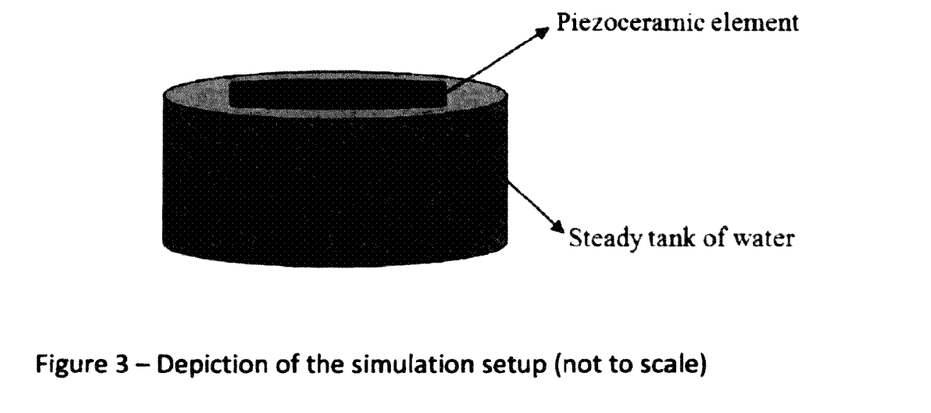
FIG. 3 shows an example of a simulation set-up.

FIG. 3 show the principle set up of the model.

Figure 4:
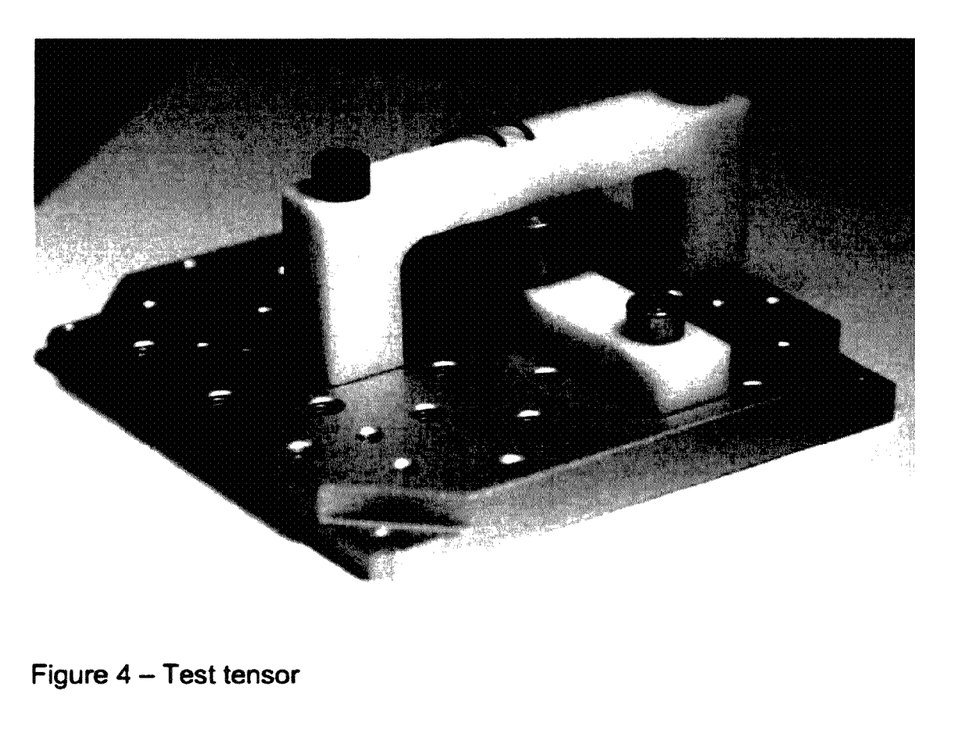
FIG. 4 shows an example of a test tensor.

After the modeling confirmed the principle, a test structure was constructed as shown in the picture of FIG. 4.

Figure 19:
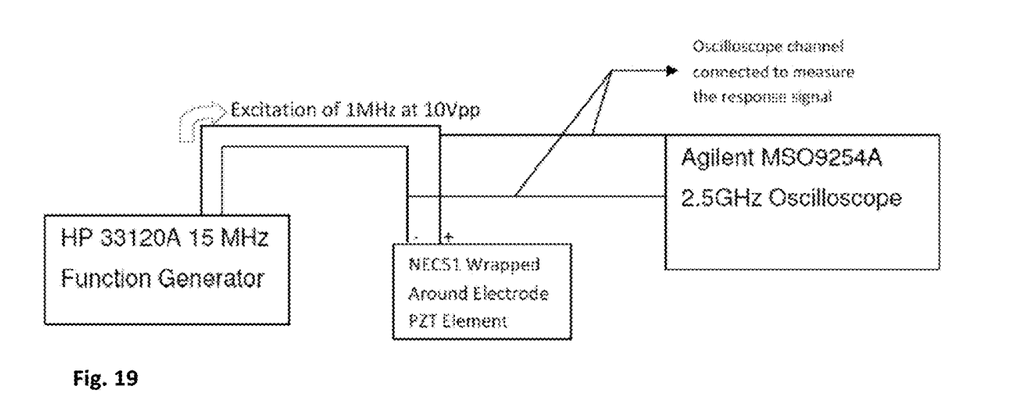
FIG. 19 is a block diagram showing a sensor hooked up to a pulse transmitter and an oscilloscope is applied to monitor.

A sensor is hooked up to a pulse transmitter and an oscilloscope is applied to monitor as shown in the block diagram in FIG. 19.

The following instruments were used for the experimental set-up:

| No. | Equipment | Details | Description |
|---|---|---|---|
| 1 | Transducer | NCE51 Wrapped around electrode (WAE) 1 MHz PZT | In contrast to the standard transducers with two terminals on two ends, WAE transducer was used to have good contact with water. |

-continued

| No. | Equipment | Details | Description |
|---|---|---|---|
| 2 | Function Generator | HP 33120A 15 MHz Function Generator | The function generator was used to supply the bursts of 1 MHz for 80 cycles at 10 Vpp. |
| 3 | Oscilloscope | Agilent MSO925A 2.5 GHz | This 20 G Sample/s sampling rate scope to 8 bit resolution was used to capture the raw response from the Transducer. |
| 4 | Source Meter | Keithly 2410 Source Meter | The precision source meter was used to supply stable current to the RTD temperature sensor. |
| 5 | Multimeter | Agilent 34410A 6 Digit Precision multimeter | The precision multimeter was used to observe the output voltage from the temperature sensor. |
| 6 | Temperature sensor | IST Innovative technology PT100 | 1/10 Din tolerance, Platinum RTD sensor was used with a temperature coefficient of 3850 ppm/° C. |
| 7 | Thermal controller | Julabo F34 thermal control pumping station | This was used to insure the temperature stability of ±0.03° C. |
| 8 | Weighing scale | Mettler Toledo PB403-S | This scale was used to dissolve salt in distilled water, to a milligram precision. |
| 9 | Purified water | 18 Mohm Pure Water | The highest standard water was used to ensure the fitting of fresh water density to temperature curve. |
| 10 | Salt | Sodium Chloride | 96% pure laboratory grade for making different density solutions. |
| 11 | Silver | Ag925 | Water container made of 92.5% pure silver and 7.5% copper. |

Figure 5:
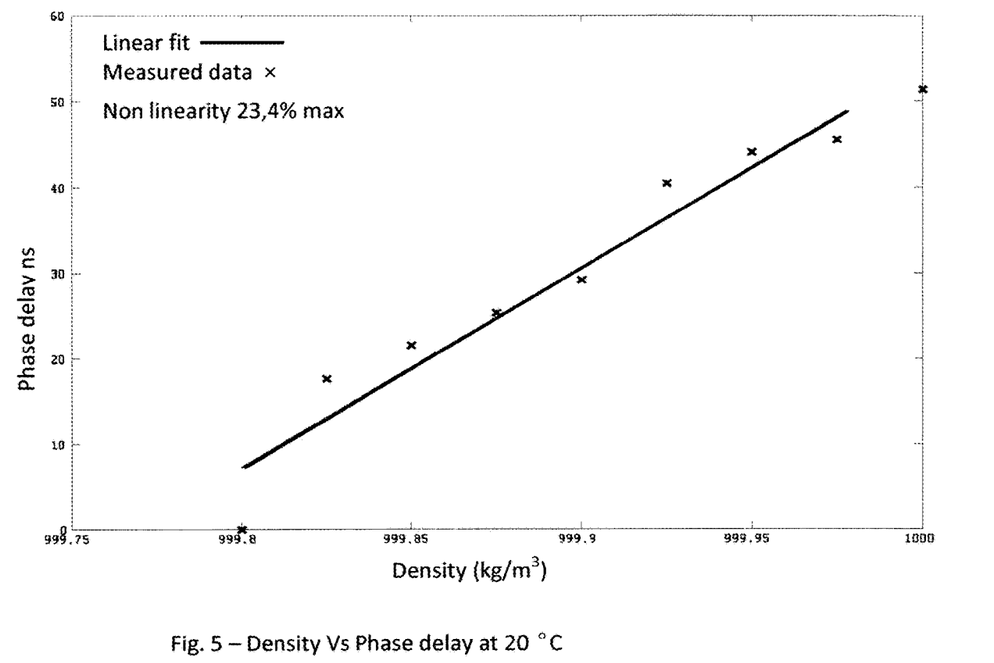
FIG. 5 is a graph showing an example of density as a function of phase delay at 20° C.

The experimental results are shown in the figures; FIG. 5 presents the density Vs phase delay plot for the solutions where the experiments were carried out at a constant temperature of 20° C., and the input parameters were used from table 1. All experiments were performed in a clean room, taking all possible precautions to minimize the environmental factors.

Figure 6:
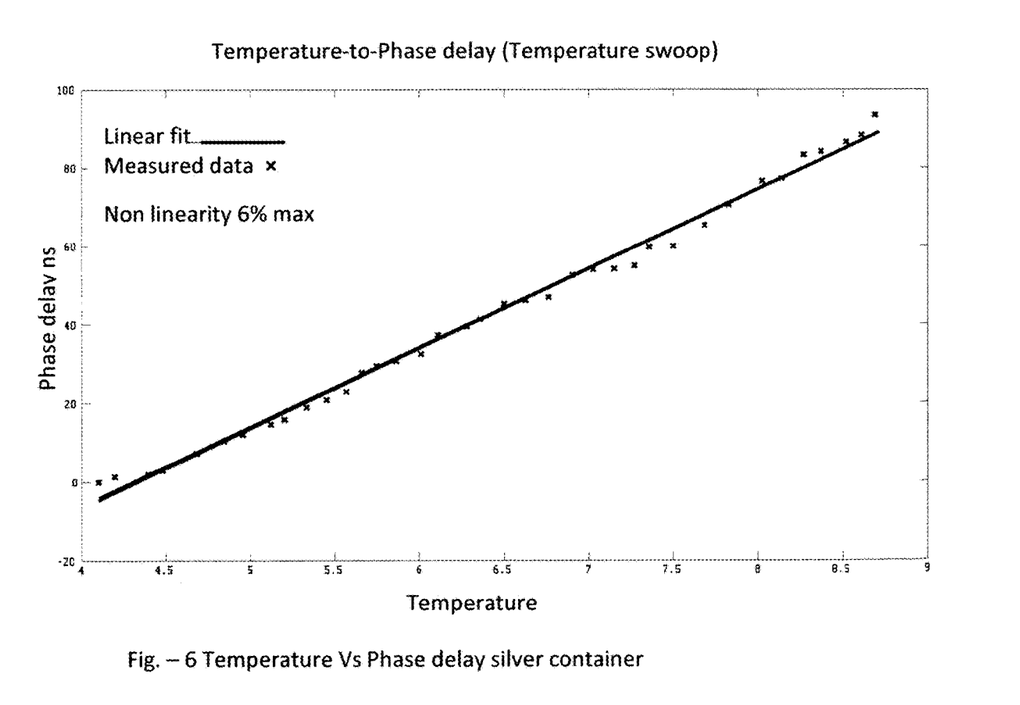
FIG. 6 is a graph showing temperature vs phase delay for a silver container.
Figure 7:
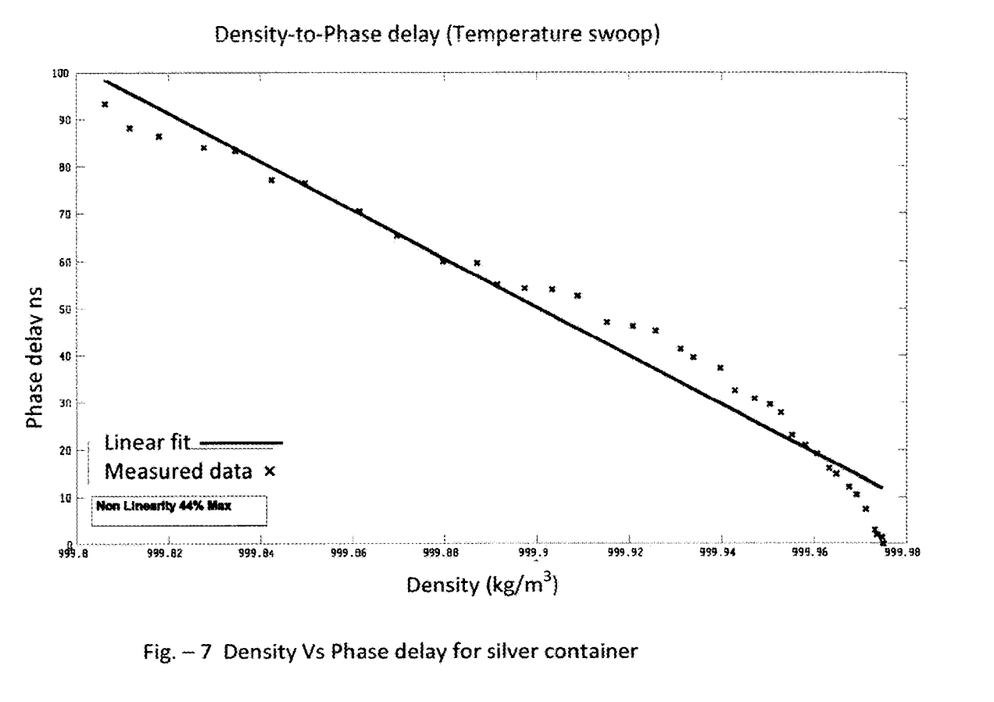
FIG. 7 is a graph showing density vs phase delay for a silver container.

The results from the second study are shown in the FIGS. 6 and 7, where the change in temperature is plotted against phase delay and change in density is plotted against phase delay, respectively. The tests were performed with water in a silver container.

Figure 8:
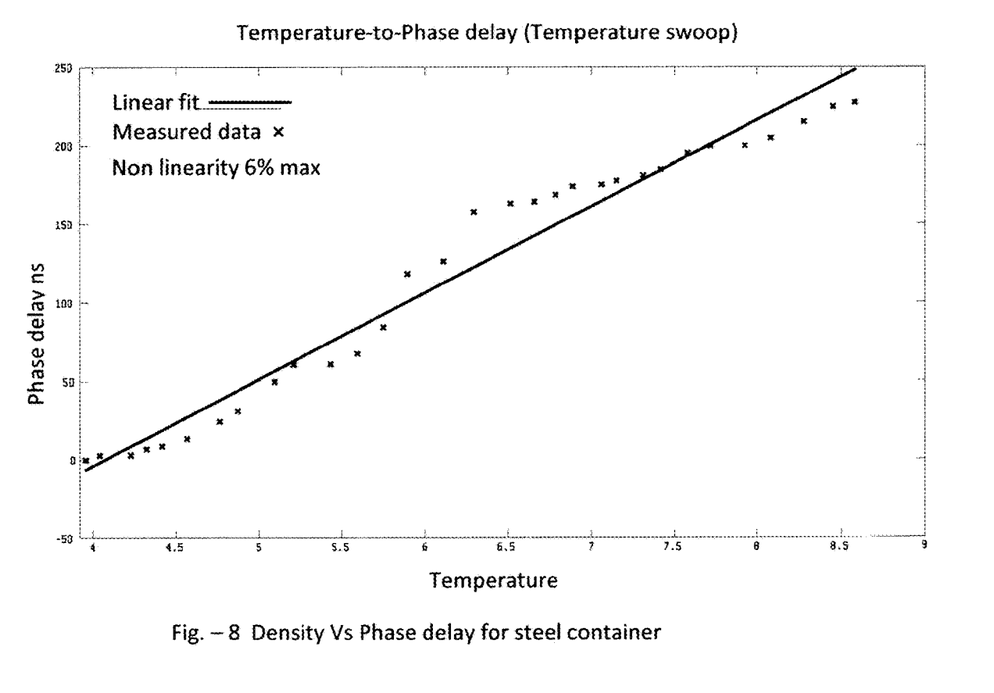
FIG. 8 shows a graph illustrating temperature vs phase delay for steel container.

The results from the third study where a stainless steel container was used for water are shown in FIG. 8. This experiment was performed to establish the effect different materials have on the transducer output. The results show that different materials are not an influential factor on the response from the PZT.

In the resultant figures the illustrated non linearity is the maximum point deviation of the measured data from the linear fit curve.

Figure 9:
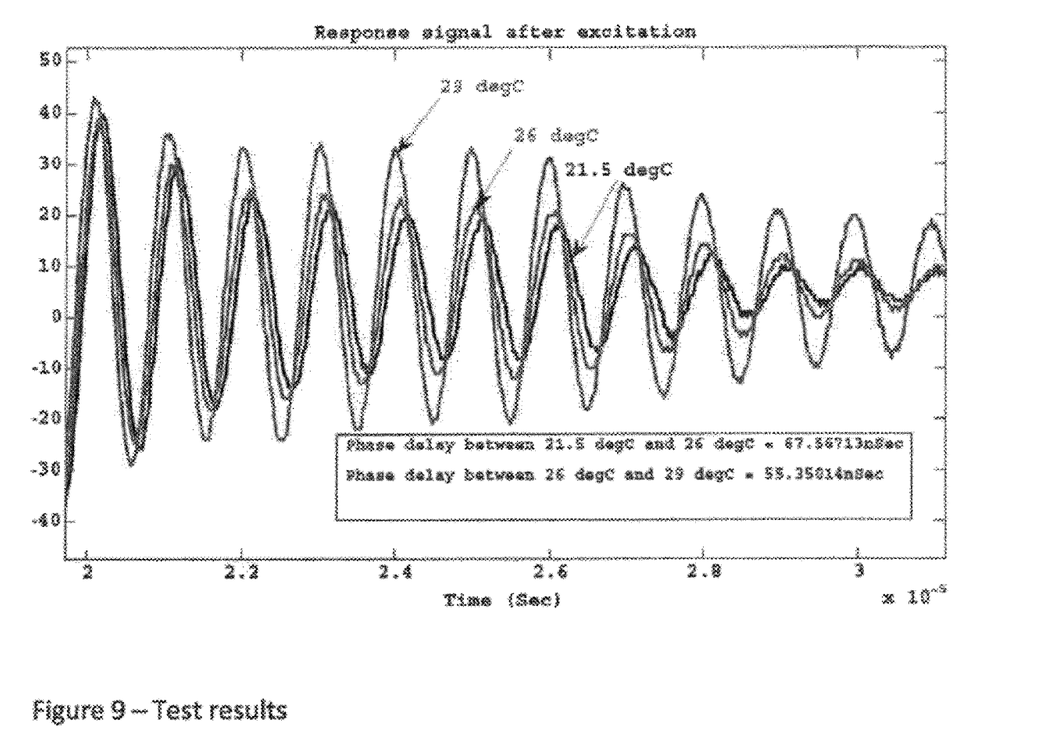
FIG. 9 shows response signal after excitation.
Figure 10:
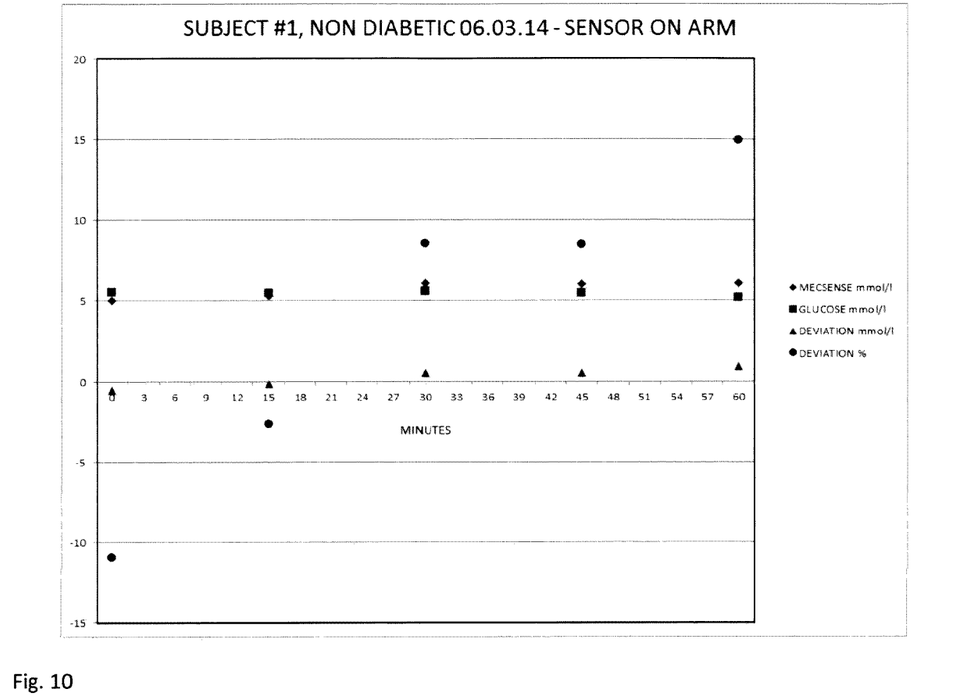
FIG. 10-18 show experimental measuring results with the present device on arm or stomach. The experimental results of the present invention (Mecsense) are correlated to convential blood sample measurements of glucose (Glucose).
Figure 11:
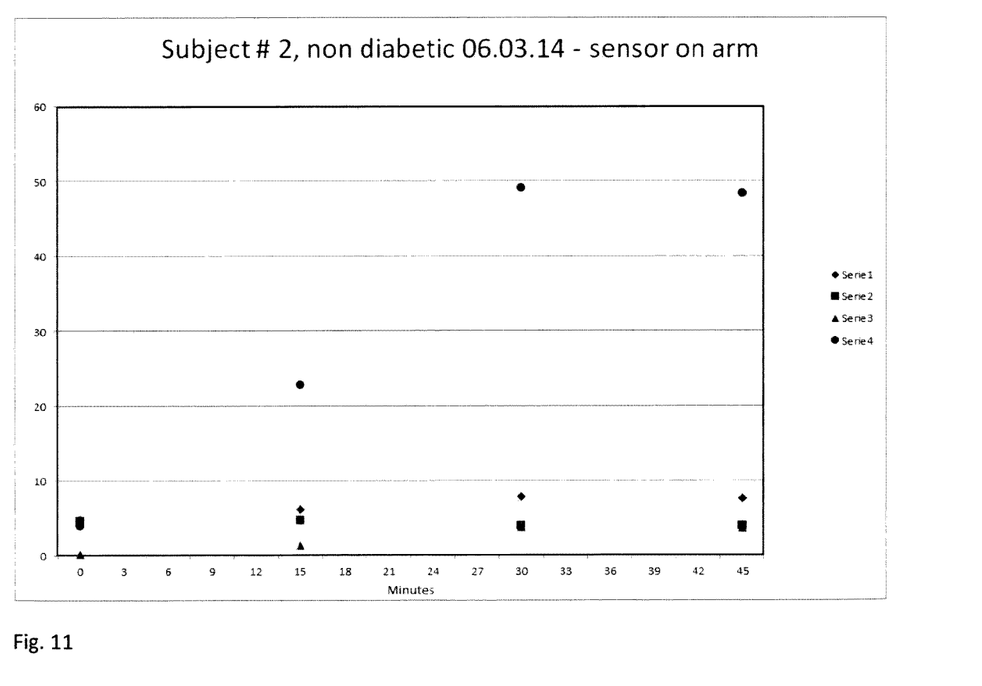
Figure 12:
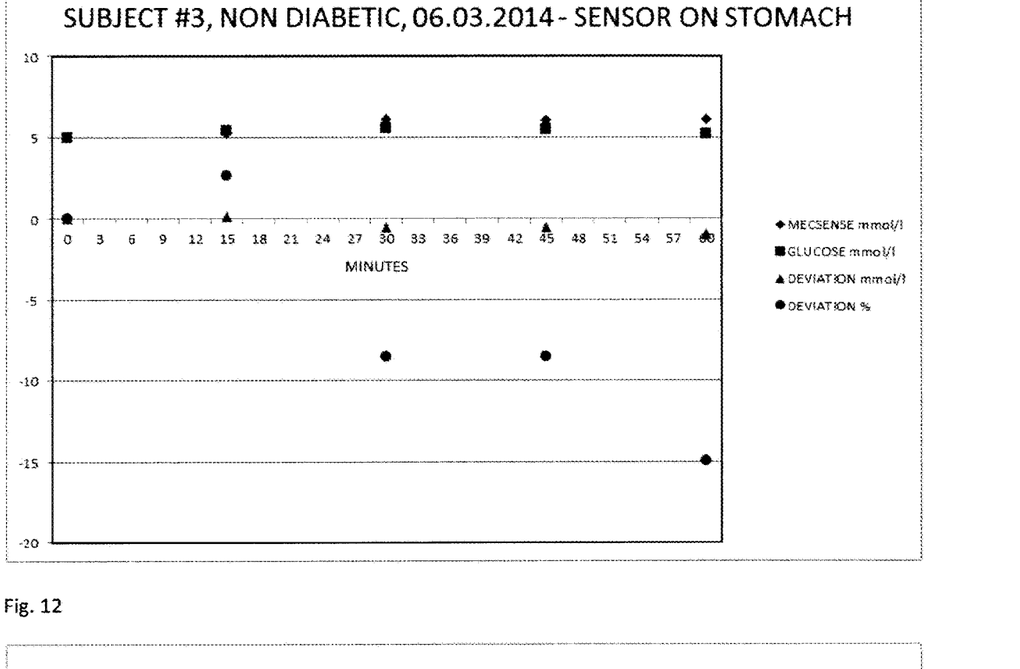
Figure 13:
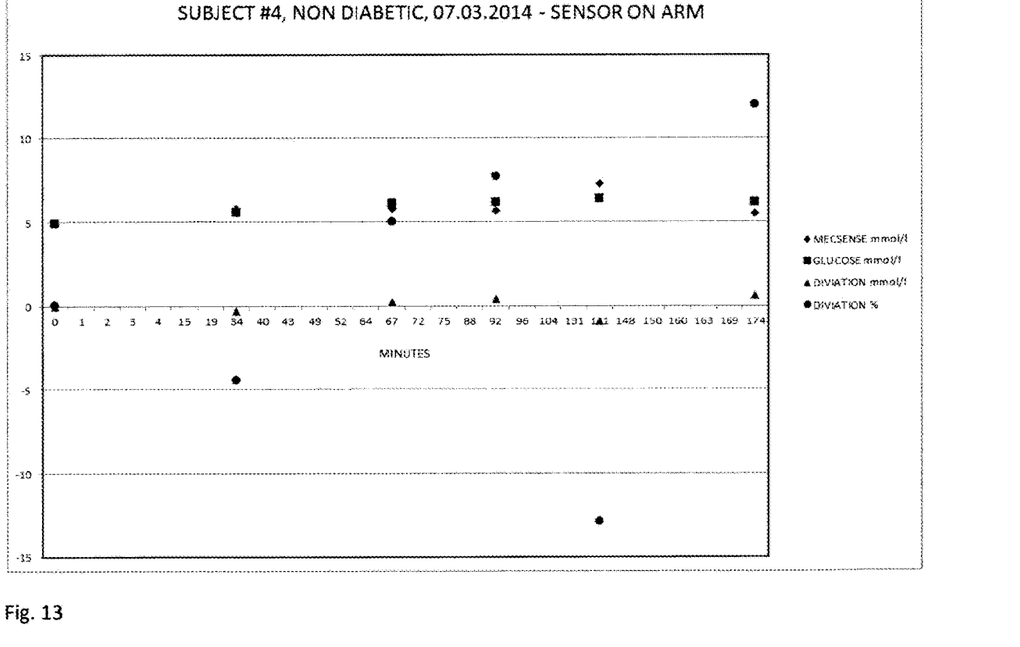
Figure 14:
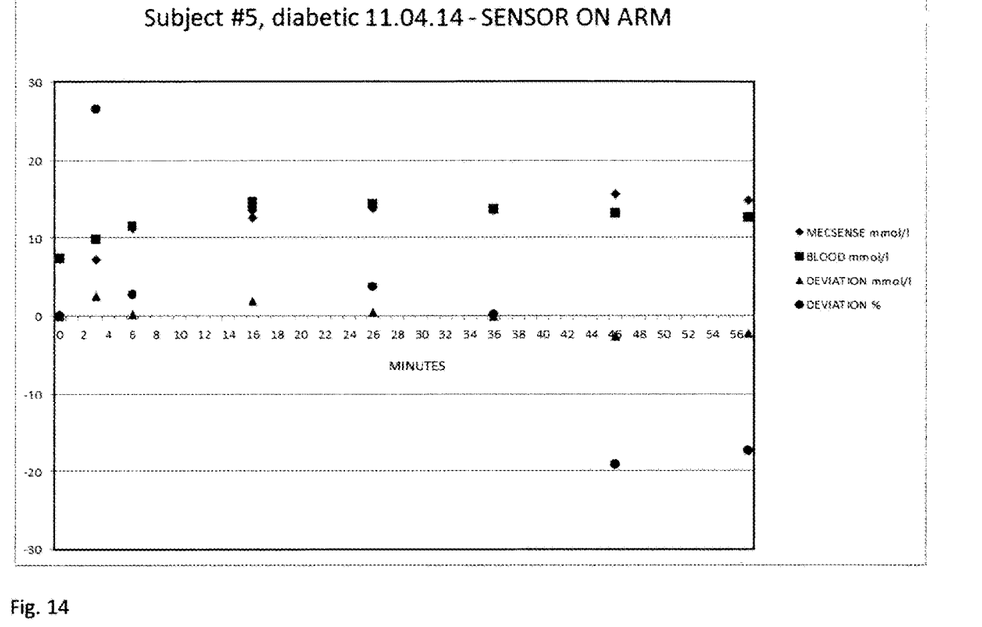
Figure 15:
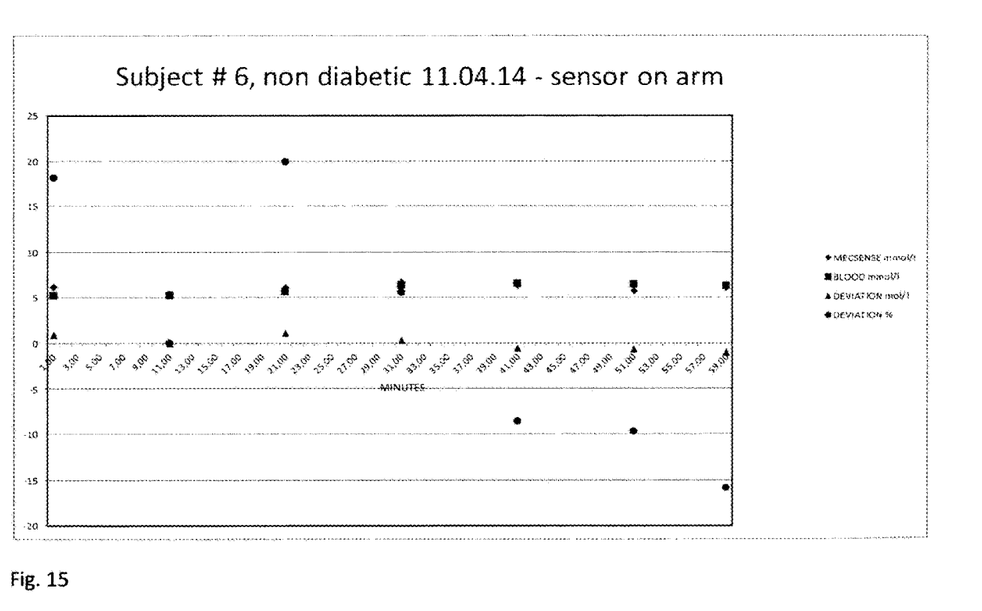
Figure 16:
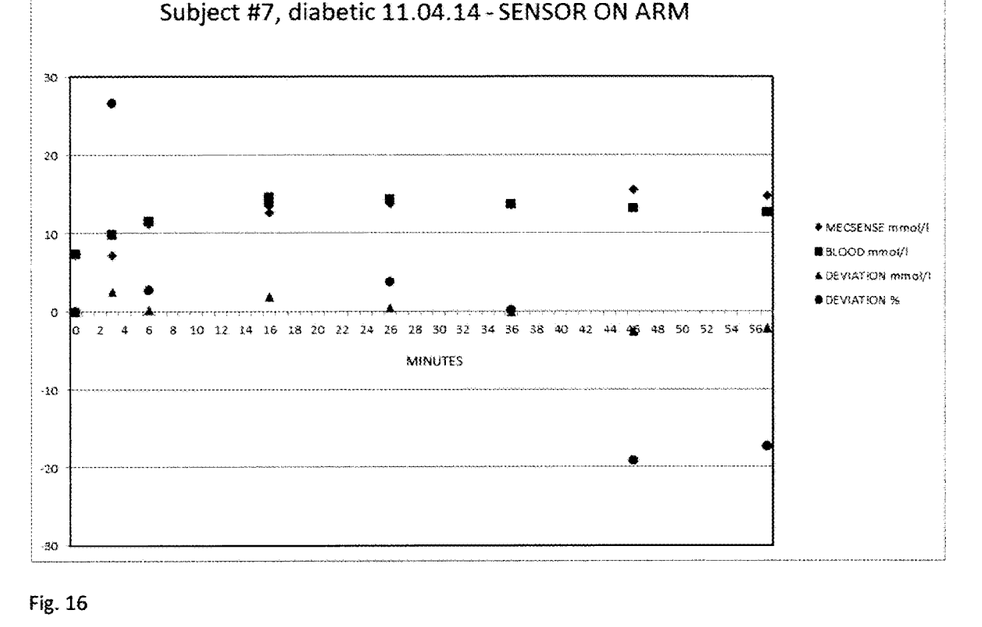
Figure 17:
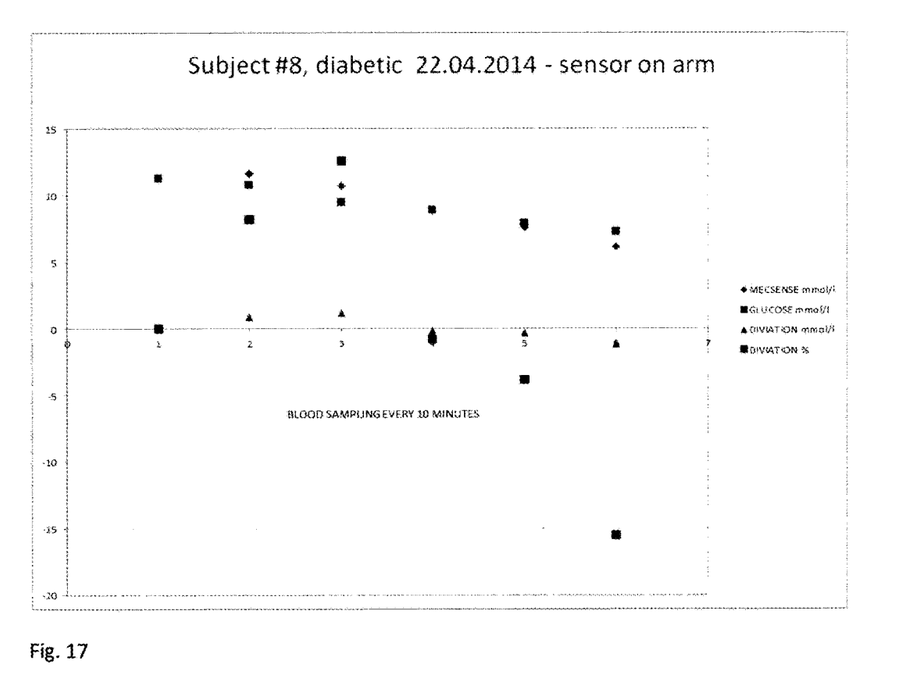
Figure 18:
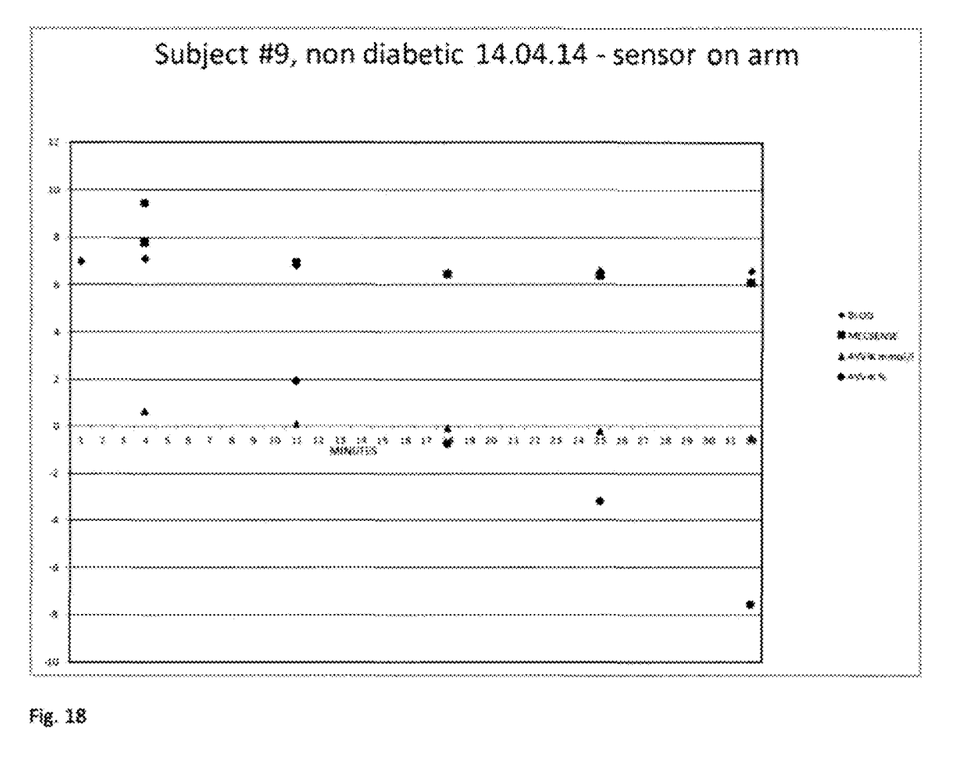

Prior to the experimental verification of the principle, a test was carried out and where the graphs shown in FIG. 9 shows the difference in phase delay and amplitude.

As can be seen there is a distinct phase shift between the curves at different temperatures. Furthermore it can also be seen that there is a distinct difference in the amplitude between the different curves.

The non-linearity from the theoretical linearity is caused by inaccuracy in the weighted salt to water.

In all studies the PZT was excited for 80 μs at 1 MHz frequency and the analysis was carried out on the response signal for 20 μs. For the excitation the voltage used was 10 Vpp, same as the voltage used in the mathematical simulation.

After verification of the principle, human trial were initiated with the sensor located in a housing and attached to the body by an elastic band.

The tests were performed on a non-diabetci human who increased the glucose level by drinking half a litre of Coca Cola and eating a slice of bread. During the test, the blood sugar was tested by Abbot's Freestyle Lite invasive glucose meter every 10 minutes.

FIG. 10-18 show experimental measuring results with the present device on arm or stomach. The experimental results of the present invention (Mecsense) are correlated to conventional blood sample measurements of glucose (Glucose). The measurements shows glucose readings as a function of time. The deviations of the two different kinds of measurements are indicated as numerical values in mmol/l and in percentage.

The invention makes it possible to show the development in the density over time, average values and how fast the density changes in either direction.

As for the measurement of the glucose level in humans the question arises if other substances changes in parallel with the glucose, and if so, how they can be mitigated.

Many substances in blood and tissue will change after a meal. Especially the heavy triglycerides could pose a challenge. Tissue buildup of proteins, extra cellular fluid and hormones could be another. So far these sources if error have been estimated to be in the magnitude of $1/10000$ to $1/1000000$ of the effect of density changes imposed by glucose.

Calculations performed on the effect of alcohol show that this is neglectable.

The density changes with temperature must be compensated for, since a 0.1° C. change in the temperature represents 0.35 mmol/liter glucose.

We have found that glucose changes in tissue have emerged theoretically as a sole and reliable parameter of tissue density changes.

Medical Evaluation of Dehydration by Hospitalized Sick and Dehydrated Patients.

By moderate dehydration (5-10%) the condition is often complicated, the heart frequency, blood pressure and heart function is modestly affected. Peripheral circulation may be reduced (capillary filling time >3 sec.), diuresis is often low and consciousness may be reduced. By severe dehydration (>10%) the patient will often have marked dehydration symtoms such as reduced consciousness, reduced skin turgor, dry mucosa, halonated eyes, tachycardia, weak pulse, tachypnea or Cheyne-Stokes respiration and oliguria and anuria.

By light dehydration in medical terms of 5% (which is 3 kg water of minimum 100 kg body weight (60% water)) and after long and hard training or gasteroenthritis, the concentration will increase in the excess of 5%. How this affect the density has to be verified by calculation. For ordinary patients this is a situation where NIGM (Non Invasive Glucose Monitoring) is not used. However, contrary to changes of glucose level, dehydration is a slow process taking hours and days whereas glucose levels can change in minutes. Thus, if dehydration takes place, glucose variation in diabetics will fluctuate over and under the mean body density caused by dehydration.

The invention is further more described in the following drawings.

Figure 1:
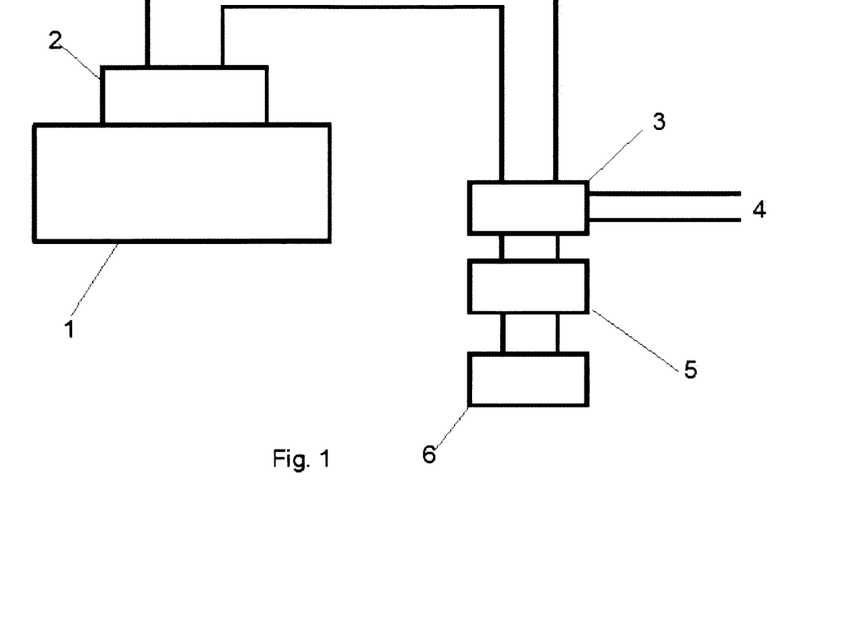
FIG. 1 shows a principle set-up of the device according to the invention.

FIG. 1 shows a principle set-up of the invention. 1) shows the body to be measured, 2) shows the PZT transducer which are generating the pulse trains, 3) is the pulse transmitter sending the electrical pulses to the PZT transducer, 4) is the power input, 5) is signal analyzer and 6) is the read out unit showing the results either as digest, graphs or a combination of these. 7) is a temperature sensor which by a mathematical algorithm compensates for the temperature on the object measured.

It is to be understood that other wiring diagrams can be applied with the objective to send a pulse train to the PZT transducer with a receiver of the reflected pulse train with an analyzer of the phase shift and difference in the amplitude.

The invention claimed is:

1. A device for continuous detection of a change of density in a fluid, wherein the device comprises:
a piezo electric transducer (PZT) comprising a pulse train generator and a pulse train transmitter configured to apply a pulse train of excitation force to a surface of the fluid; said PZT further configured to sense a dying pulse train that decays after the applied pulse train of excitation force is stopped,
wherein the PZT is configured to undergo a response voltage due to a reverse piezoelectric effect when the applied pulse train is stopped, wherein the reverse piezoelectric effect is an effect on the PZT by the dying pulse train, and
wherein the PZT is configured to generate a pulse train in response to the dying pulse train in the fluid that has a phase shift and a change in amplitude compared to the train of excitation force initially applied to the surface of the fluid;
a power input;
a signal analyzer configured to analyze the change in phase shift and amplitude of the applied pulse train compared to the generated pulse train; and
a read out unit configured to show results of said change in phase shift and amplitude.

2. The device according to claim 1, wherein the pulse train generator is configured to generate a pulse train selected from the group consisting of a sinus pulse, a square pulse and a step pulse.

3. The device according to claim 2, wherein the pulse train generator is configured to generate a sinus pulse.

4. A method of monitoring a change in density of a body liquid caused by a change of a solute in the body liquid comprising providing the device according to claim 1.

5. The method according to claim 4, wherein the change of the solute in the body liquid is a change of a glucose level in the body liquid.

6. The method according to claim 4, wherein the change of the solute in the body liquid is a change of an alcohol level in the body liquid.

7. The method according to claim 4, wherein a change of dehydration is monitored.

8. A method of monitoring a change of density of a beverage comprising providing the device according to claim 1.

9. A method of monitoring a change of density of a wood or a wood product comprising providing the device according to claim 1.

10. A method of monitoring density of an oil comprising providing the device according to claim 1.

11. The method according to claim 8, wherein the beverage is a wine or a liquor.

12. A method for continuous detection of a change of density of a fluid, comprising:
applying an ingoing fixed pulse train of excitation force transmitted from a PZT to a surface of the fluid;
stopping application of the pulse train of excitation force;
sensing a dying pulse train from the fluid, wherein the dying pulse train decays after the applied pulse train of excitation force is stopped;
producing a generated pulse train by the PZT in response to the dying pulse train,
wherein the PZT is configured to undergo a response voltage due to a reverse piezoelectric effect when the applied pulse train is stopped, wherein the reverse piezoelectric effect is an effect on the PZT by the dying pulse train, and
wherein the PZT is configured to generate a pulse train in response to the dying pulse train in the fluid that has a phase shift and a change in amplitude compared to the train of excitation force initially applied to the surface of the fluid;
receiving the generated pulse train from the PZT in response to the dying pulse train in the fluid after the ingoing fixed pulse train of excitation force is stopped, and
monitoring a change in a phase shift and an amplitude between the ingoing fixed pulse train and the generated pulse train.

13. The method according to claim 12, wherein the ingoing fixed pulse train generated is selected from the group consisting of a sinus pulse train, a square pulse train and a step pulse train.

14. The method according to claim 12, wherein the ingoing fixed pulse train is a sinus pulse train.

15. The method according to claim 12, further comprising showing the results of said change in the phase shift and the amplitude.

* * * * *